(12) United States Patent
Bucher

(10) Patent No.: US 8,114,360 B2
(45) Date of Patent: Feb. 14, 2012

(54) ONE-WAY FRACTIONATING DEVICE

(75) Inventor: Franz Gregor Bucher, Zug (CH)

(73) Assignee: Medic Tools AG, Zug (CH)

( * ) Notice: Subject to any disclaimer, the term of this patent is extended or adjusted under 35 U.S.C. 154(b) by 938 days.

(21) Appl. No.: 11/577,839

(22) PCT Filed: Nov. 18, 2005

(86) PCT No.: PCT/CH2005/000684
§ 371 (c)(1),
(2), (4) Date: Apr. 24, 2007

(87) PCT Pub. No.: WO2006/076819
PCT Pub. Date: Jul. 27, 2006

(65) Prior Publication Data
US 2007/0248499 A1    Oct. 25, 2007

(30) Foreign Application Priority Data
Jan. 21, 2005    (CH) ........................... 0091/05

(51) Int. Cl.
*G01N 1/28* (2006.01)
(52) U.S. Cl. .......................... 422/500; 241/100
(58) Field of Classification Search ............ 422/99–102, 422/500, 547, 549, 550, 559; 241/100
See application file for complete search history.

(56) References Cited

U.S. PATENT DOCUMENTS

| | | | | |
|---|---|---|---|---|
| 3,136,491 A | * | 6/1964 | Posmanter | 241/169.1 |
| 3,796,542 A | * | 3/1974 | Kline | 436/177 |
| 3,827,640 A | * | 8/1974 | Marrie | 241/100 |
| 4,307,808 A | * | 12/1981 | Johnson | 209/614 |
| 4,343,437 A | * | 8/1982 | Czelen | 241/169.1 |
| 2002/0092941 A1 | * | 7/2002 | Henderson et al. | 241/169.1 |
| 2002/0130208 A1 | * | 9/2002 | Pedersen | 241/169.1 |
| 2004/0018120 A1 | * | 1/2004 | Rappin et al. | 422/101 |

FOREIGN PATENT DOCUMENTS

| | | |
|---|---|---|
| EP | 0590219 | 10/1992 |
| GB | 2374301 | 10/2002 |
| JP | 02098355 | 4/1990 |
| WO | 2004035191 | 4/2004 |

* cited by examiner

*Primary Examiner* — Jan Ludlow
(74) *Attorney, Agent, or Firm* — Volpe and Koenig, P.C.

(57) ABSTRACT

A single-use fractionating device (53) is provided including a laboratory test container (43) for the substances to be fractioned (55), and a receiving container (27) for receiving fractioned substances (57). The containers (27, 43) are interconnected by the fractionating device (53). For the fractionating process, the two containers (27, 43) or the fractionating mechanism (1) with the laboratory container (43) and the fractionating mechanism body (11) with the receiving container (27) are rotated relative to each other. The product to be fractioned is hermetically sealed from the environment during the entire fractionating process.

7 Claims, 4 Drawing Sheets

ONE-WAY FRACTIONATING DEVICE

BACKGROUND

The subject of the invention is a single-use fractionating device for fractionating or fragmenting substances.

Multiple use fractionating devices are generally known and used in laboratory processing. When fractionating and fragmenting herbal substances and tissue material in not hermetically sealed vessels and using conventional, reusable fractioners and fragmenters there is the latent risk of cross-contamination from one charge of material to be fractioned to the next, between the substance to be fractioned and the user executing the processing as well as the contamination of a sterile material to be fragmented by the environment.

From WO 2004/035191 a single-use mixer and homogenizer is known, which can be screwed onto a laboratory test vessel and can mix and homogenize a substance inserted into a laboratory test vessel, however it can also mill it by the knives and corresponding counter knives, i.e. fractionating. This known device is excellently suitable for mixing, however, when used as a fractioner it is not ensured that, after a predetermined fractionating period, the entire content has reached the desired even grain size, particularly when exceeding a certain amount.

SUMMARY

The object of the present invention is the creation of a single-use fractionating device, allowing the fractionating and fragmenting process to occur, after the insertion of the substance to be fractioned, hermetically sealed from the environment.

This object is attained by a single-use fractionating device according to the invention. Particularly advantageous embodiments of the invention are described below.

By the arrangement of the fractionating housing at a first laboratory test vessel with a substance to be fractioned and the arrangement of the fractionating device on a second laboratory test vessel, with the fractionating device being rotationally supported in the fractionating housing, it is possible for the substance to be fractioned while passing, i.e. the already fractioned substance to be fractioned does not enter the fractionating device for a second time. In this manner, the desired grain size is achieved and it is always discernible when the fractionating process will be completed. In a particularly advantageous embodiment, the level of fractionating can be adjusted.

BRIEF DESCRIPTION OF THE DRAWINGS

In the following the invention is explained in greater detail using an illustrated exemplary embodiment. Shown are.

BRIEF DESCRIPTION OF THE PREFERRED EMBODIMENTS

Figure 1:
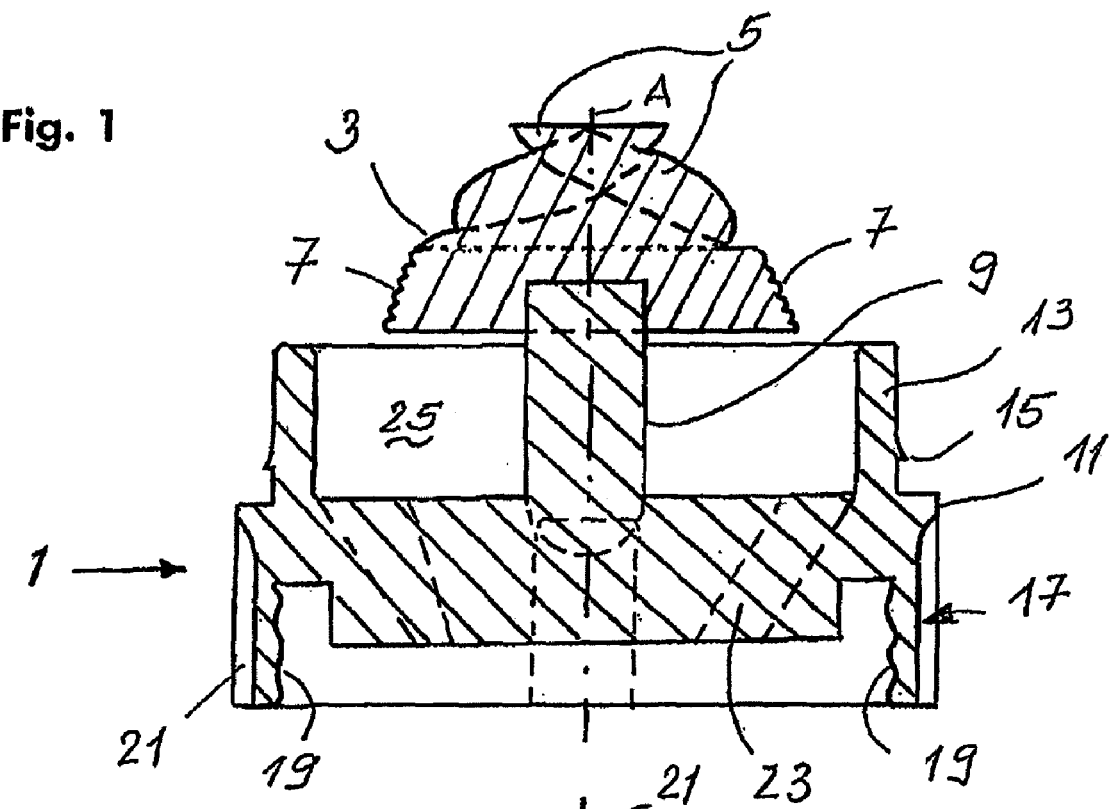
FIG. 1 an axial cross-sectional view through the fractionating device and the connection flanges for the second laboratory test vessel, FIG. 2 a top view of the fractionating device, FIG. 3 an axial cross-sectional view through the housing of the fractionating device and the connection flange for the first laboratory test vessel, FIG. 4 a top view on the housing, and FIG. 5 an axial cross-sectional view through the assembled single-use fractionating device, FIG. 6 an axial cross-sectional view through another exemplary embodiment of the housing of the fractionating device, FIG. 7 an axial cross-sectional view through the fractionating device and a connection flange for the second laboratory test vessel according to FIG. 6.
Figure 2:
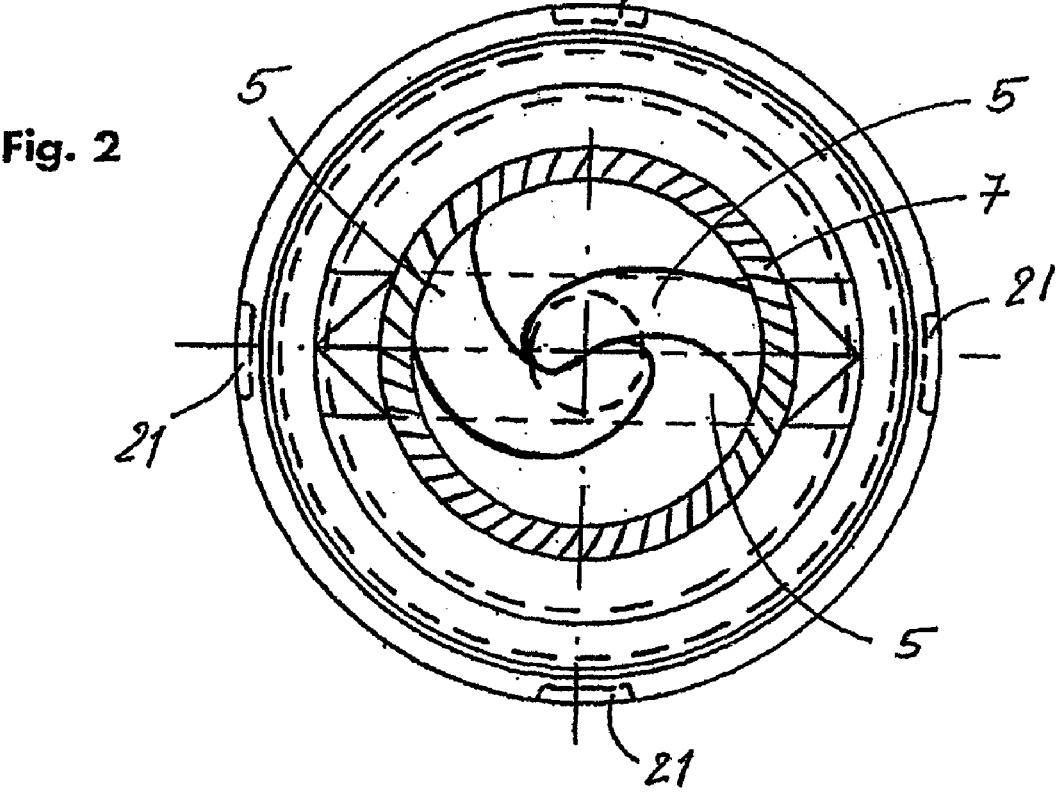

In FIG. 1, a fractionating device is marked with the reference character 1, which is provided with a fractionating head 3 with, for example, two feeding screws 5 and with a frustum-shaped cutting element 7. The individual blades of the cutting elements 7 may be positioned diagonally, as discernible in FIG. 2. Of course, a different cutting geometry is also possible. The fractionating head 3 is positioned on a shaft stump 9, mounted to the body 11 of the fractionating device. At the body 11 of the fractionating device, at the side of its head, a collar 13 facing upwards is provided with a circumferential retaining rib 15. At the bottom of the body 11 of the fractionating device a flange 17 is formed having an internal thread 19. Axially extending grooves 21 are provided on the outside surface of the flange 17. Inside the collar 13 in the body 11 of the fractionating device, recesses 23 are provided that penetrate therethrough. These recesses 23 connect the space 25 located between the cutting element 7 and the surface of the body 11 of the fractionating device with the bottom of the body 11 of the fractionating device. The interior thread 19 of the flange 17 serves to fasten a laboratory test vessel as a collection vessel 27 for the fractioned substance 57. The collection vessel 27 is provided at its upper brim with a respectively embodied exterior thread 29. On the one side, it interfaces with the inside thread 19 and, when screwed in completely, contacts the body 11 of the fractionating device in a sealing manner.

Alternative to a threaded connection between the collection vessel 27 and a food container 43, e.g. laboratory test vessel, and the body 11 of the fractionating device and/or the fractionating device 1, a snap-action device may also be used. Instead of the interior thread 19, 41, then there are grooves or punctures 119, 141 (cf. FIGS. 6 and 7) and the exterior thread there is replaced by beads at the vessels 27, 43 (no figure).

Figure 3:
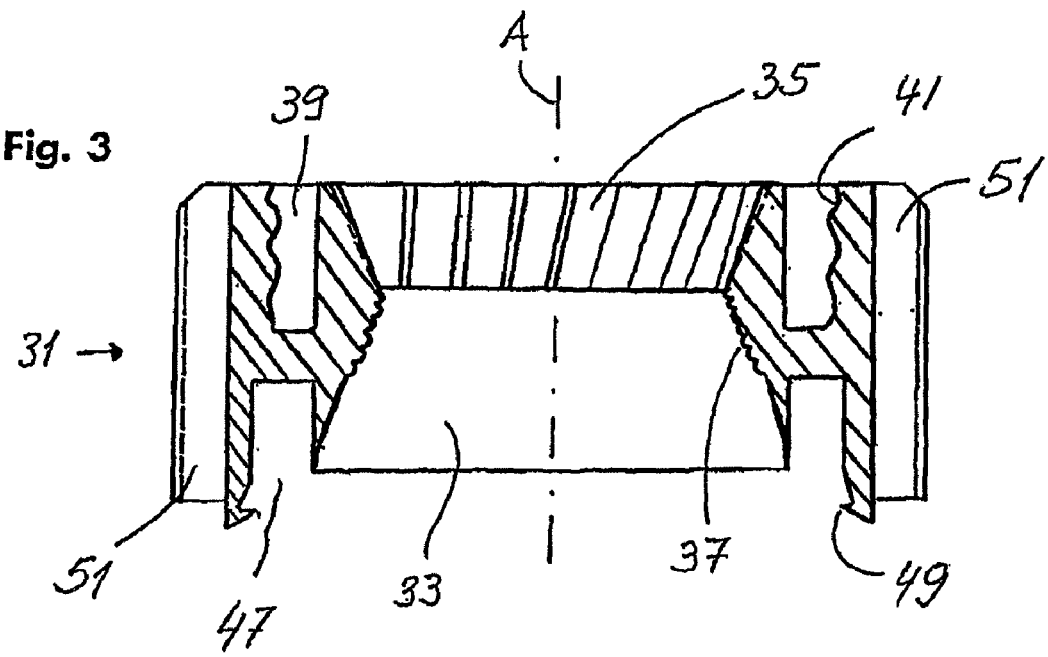
Figure 4:
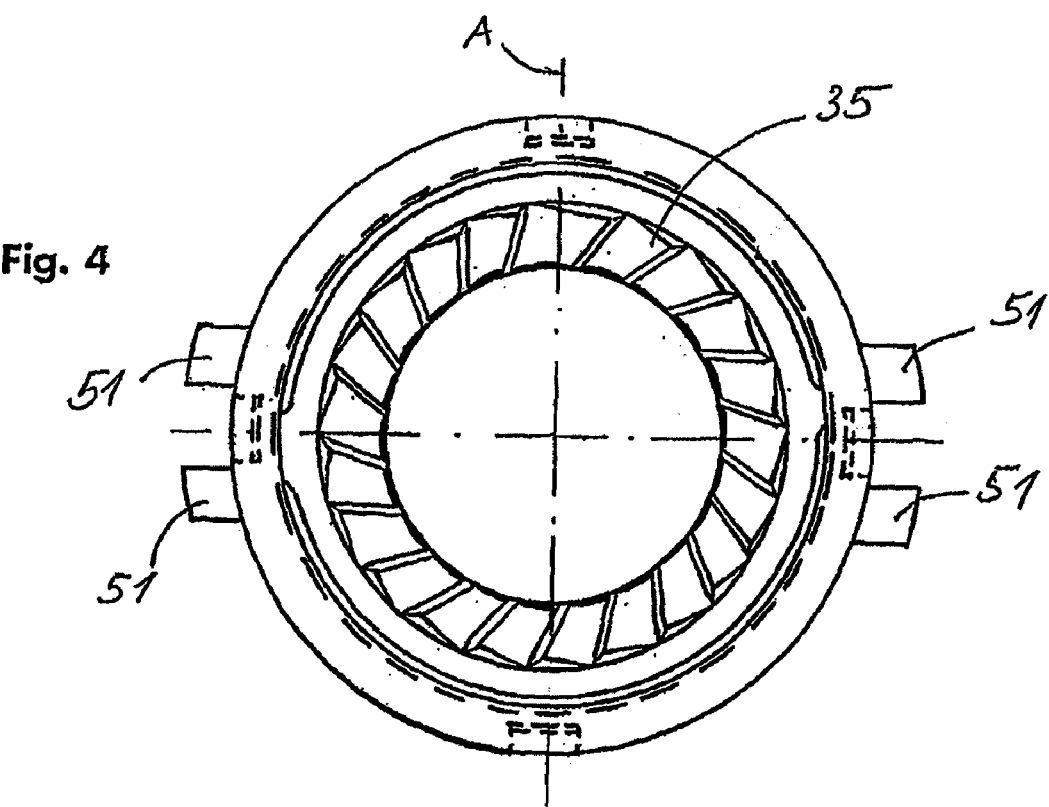

In the FIGS. 3 and 4, the housing 31 of the fractionating device 1 is shown. This comprises a double-cone shaped opening 33, with at the periphery a multitude of guide elements 35 being provided at the top and cutting elements 37 at the bottom. The cone shape of the opening in the area of the cutting elements 37 is approximately equivalent to that of the cutting elements of the fractionating head 3. Outside the double-cone shaped opening 33 there is a circular groove 39 that extends from the top into the housing 31, with an interior thread 41 being embodied at its exterior side. This thread engages a laboratory test vessel 43, serving as a food container, and/or an external thread 45 mounted at its brim. Inserted at the bottom of the housing 31 there is a second encircling groove 47 with an encircling snap-action rib 49 being formed at its exterior side. Pairs of axially extending reception ribs 21 are formed at the periphery of the housing 31.

Figure 6:
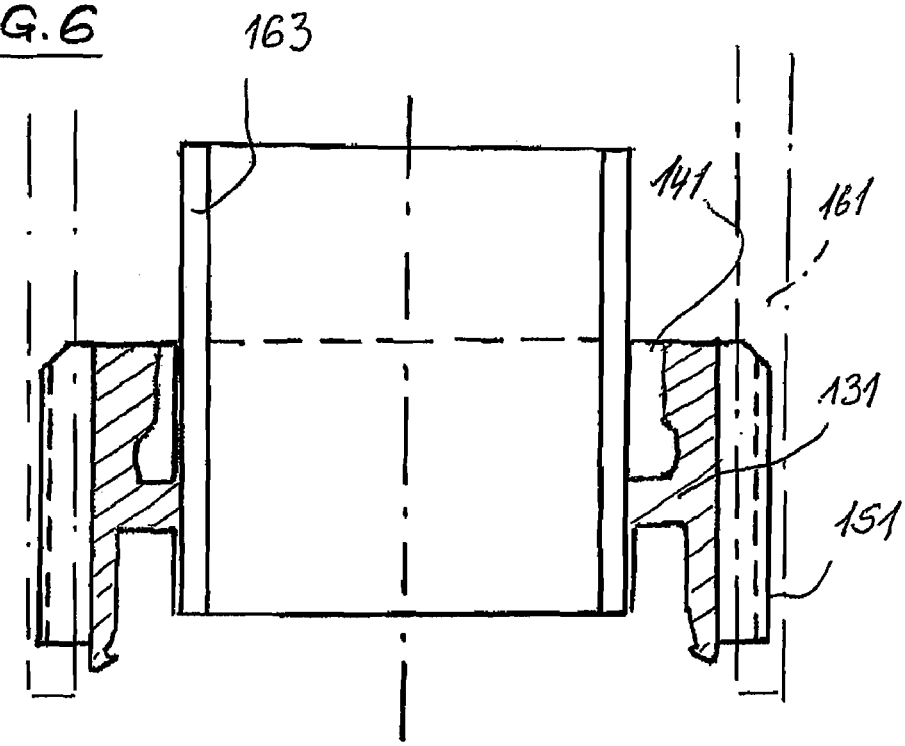

The reception ribs 51, 151 face each other axially symmetrically and serve to engage holding means 161, which prevent a torsion of the body 31, 131 of the fractionating device (cf. also FIGS. 6/7)

Figure 5:
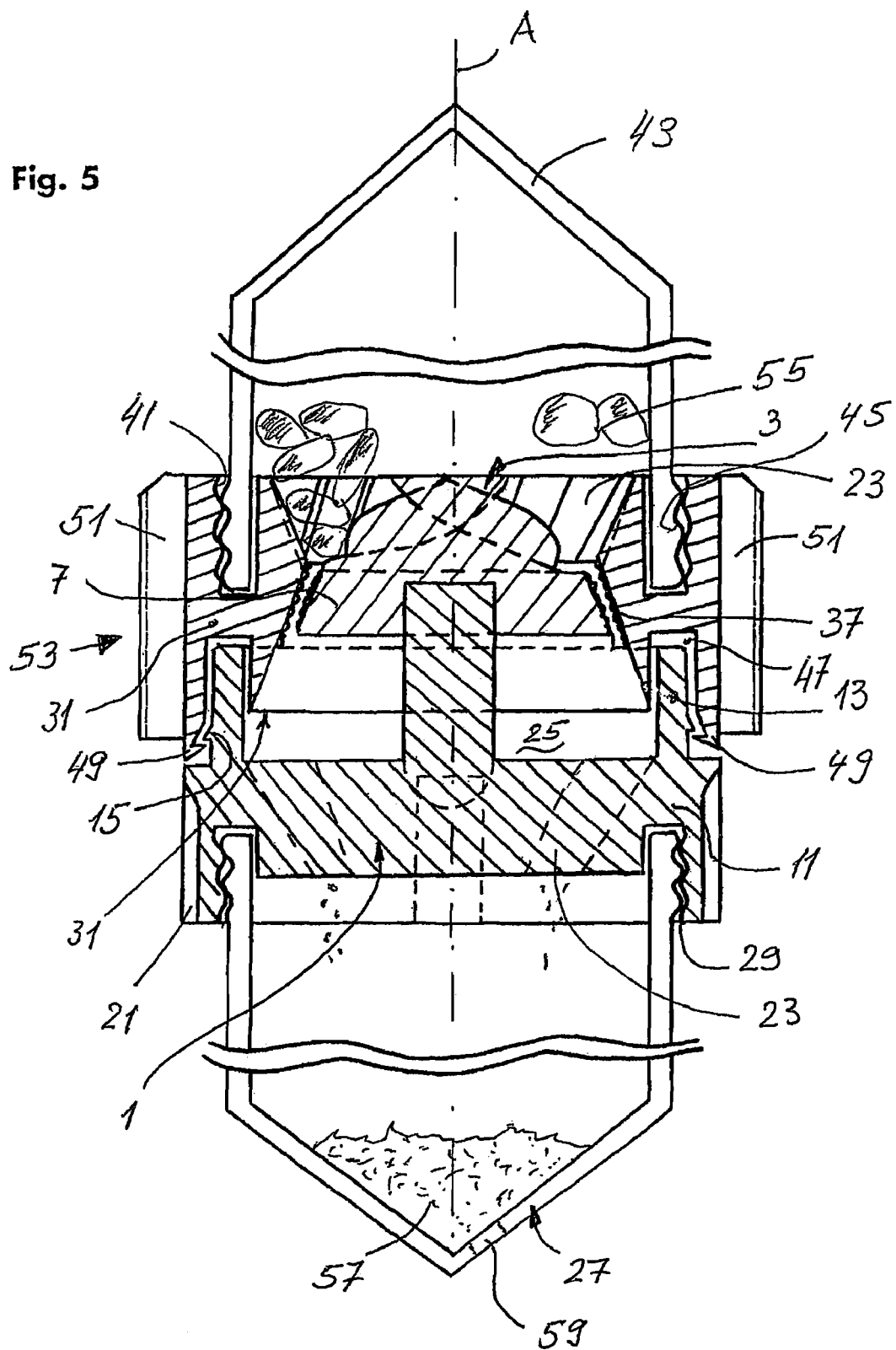

FIG. 5 shows the completely assembled single-use fractionating device 53. Here, it is discernible that the fractionating device 1 is placed directly on the opening of the collection vessel 27 and the housing 31 for the fractionating device 1 on the opening of the food container 43. The fractionating device 1 and the housing 31 are held together by the snap-action ribs 15 at the fractionating device and the snap-action rib 49 at the housing 31. The connection of these two parts is provided such that a mutual rotary motion around the longitudinal axis A can occur. This means, the collar 13 at the fractionating device 1 rests in the groove 47 at the housing 31 with some play.

In the laboratory test vessel 43, schematically the substances to be fractioned are marked with reference character 55 and in the collecting vessel the fractioned substances with the reference character 57.

Figure 7:
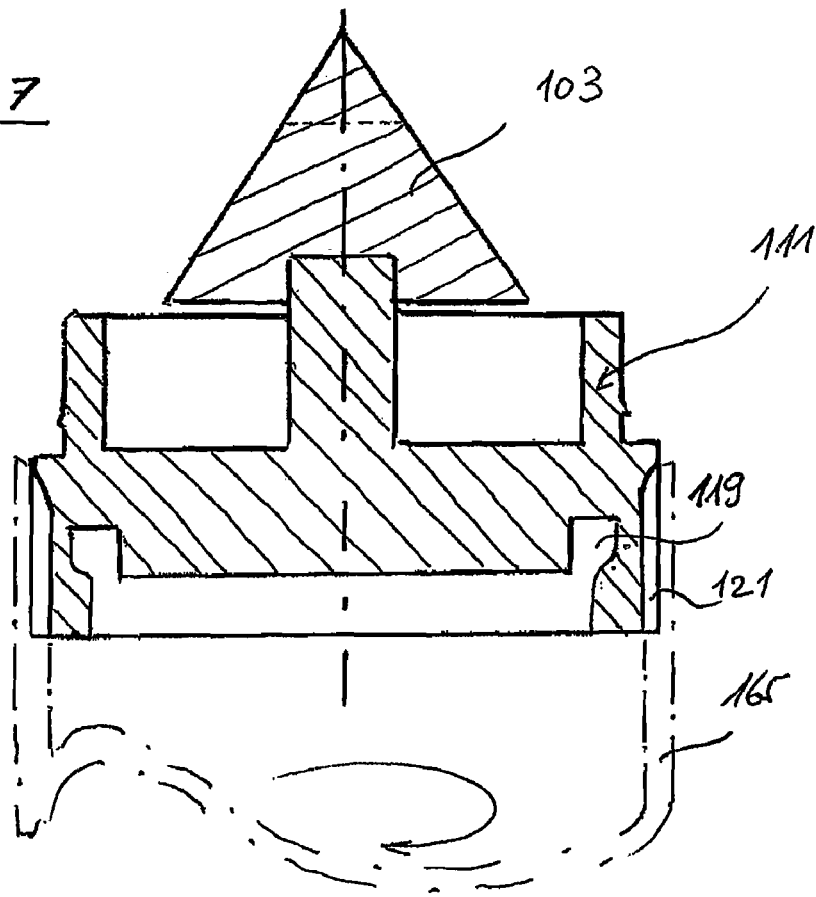

In another embodiment of the invention, according to FIGS. 6 and 7, a cylindrical bore in a tube 163 made from metal or another hard plastic is provided instead of the double-cone shaped opening 33 in the housing 131.

The surface of the bore is either grooved, screened, knurled, or roughened in any other fashion. The corresponding fractionating head 103 at the fractionating device 101 may have the shape of a cone, frustum, or a pyramid with a multi-faceted base. The diameter of the base of the cone of the pyramid is smaller than the interior diameter of the tube 163 by the respective grain size to be achieved.

In the following, the fractionating process is described. At the sampling site, e.g., on a ship, at a sack, or a silo, unfractioned substances 55, e.g., cereal grains, are filled into the laboratory test vessels 43. Subsequently the housing 31 is screwed from the top onto the laboratory test vessel 43 with the fractionating device 1 and the collection vessel 37 mounted thereto and thus hermetically sealed. Prior to fractionating, the fractionating device 53 is rotated into the position shown in FIG. 5, so that the laboratory test vessel 43 is upside down. Subsequently the fractionating device 53 is placed onto a suitable drive 165 in the laboratory. It engages in a form-fitting manner the grooves 21, 121 at the fractionating device 1 from the bottom. From the top a snap-action element 161 engages the reception ribs 51, 151, which prevent a rotation of the housing 31, 131. When the drive 165 of the fractionating drive 1 is made to rotate together with the collection vessel 27 the substances 55 are guided to the cutting elements 7 and 37 by the feeding screw 5 or the frustum 105, and here constantly fractioned while passing. The substance 57 to be fractioned enters the space 25 and therefrom it reaches the collection vessel 27 through the recesses 23 in the body 11 of the fractionating device. Here, after the connection between the collection vessel 27 and the body 11 of the fractionating device is loosened, it can be removed.

During the entire fractionating process neither contaminates can enter from the outside into the substance to be fractioned nor can the substance to be fractioned exit from the fractionating device 53. Unfractioned substances 55 and unused fractioned substance 57 can be disposed together with the fractionating device after use.

Of course, alternatively the housing 31 with the laboratory test vessel 43 can be made to rotate via the accepting ribs 51 and the fractionating device 1 with the collection vessel being fixed in a torque-proof manner.

The fractionating head 3 with the cutting elements 7 may be axially adjusted in another embodiment of the invention. By axial displacement, the distance between the cutting elements 7 and the cutting elements 37 at the housing 31 can be adjusted and changed. This way the fineness, i.e. the level of fractionating, can be adjusted.

In another advantageous embodiment, for the purpose of removing the fractioned substance 57 the wall of the collecting vessel 27 can be provided at one site with a penetration area 59, e.g., with a membrane through which a pipette or another removal device can be guided.

The fractionating device 53, depending on the size, can be provided with food and/or collection vessels 27, in which few cubic centimeters of fractioned substance 55 can be contained; however, it may also have a dimension in which for example one kilogram of cereal grains to be fractioned can be collected and fractioned. The entire fractionating device 53 is cost-effectively made from plastic or cost-effective metal elements.

The invention claimed is:

1. A single-use fractionating device (53) for fractionating or fragmenting genetically altered, infectious, malodorous, chemically corrosive, or other substances (55) to be kept sterile, comprising a fractionating device (1) inserted between openings of first and second vessels or laboratory test vessels (27, 43) located axially over top of each other, with the first vessel (27) being connected to a fractionating head (3) via a body (11) and the second vessel (43) being connected with a housing (31) of the fractionating device that cooperates with the fractionating head (3), and the fractionating head (3) connected to the first vessel (27) is rotated around an axis (A) in reference to the second vessel (43) and the housing (31) of the fractionating device such that passage of the substances between the fractionating head (3) and the housing (31) due to the rotation causes fractionation of the substances, and at the body (11) of the fractionating device, a dually conical opening is provided, with the fractionating head (3) engaging from a bottom thereof with a frustum-shaped cutting element (7) and cooperating with a feeding screw (5) supported by the fractionating head (3) at a top thereof, the feeding screw having a tapered thread that expands from the top thereof toward the frustum-shaped cutting element.

2. A single-use fractionating device according to claim 1, wherein the fractionating head (3) is arranged on the body (11) of the fractionating device, which is disc-shaped, in a rotation-proof manner and set axially at a distance therefrom and recesses (23) are provided in the body (11) of the fractionating device, which create a connection between the fractionating head (3) and the first vessel (27) mounted to the body (11) of the fractionating device.

3. A single-use fractionating device according to claim 1, wherein a top face of the housing (31) of the fractionating device is provided with a first groove (39) for inserting or snapping the second vessel (43) and a bottom face of the housing (31) is provided with a second groove (47) for inserting and for rotationally supporting a collar (13) mounted to the body (11) that supports the fractionating head (3) of the fractionating device.

4. A single-use fractionating device according to claim 3, wherein on a periphery of the collar (13), a first snap-action rib (15) is provided, which cooperates with a second snap-action rib (49) on an exterior side of the second groove (47) and connects the fractionating head (3, 103) to the housing (31, 131) in a rotary manner.

5. A single-use fractionating device according to claim 1, wherein the housing (131) of the fractionating device (101) comprises a cylindrical bore in a tubular section, the bore engageable with the fractionating head of the fractionating device, the fractionating head having the shape of a cone, frustum, or pyramid.

6. A single-use fractionating device according to claim 1, wherein an area (59) that can be pierced is provided on the first vessel (27) for the fragmented substance (57) for removing the fragmented substances (57).

7. A single-use fractionating device according to claim 1, wherein the vessels (27, 43) are connected to the fractionating device (1, 131) via snap-action connectors.

* * * * *